(12) United States Patent
Wada et al.

(10) Patent No.: US 8,663,716 B2
(45) Date of Patent: Mar. 4, 2014

(54) COMPOSITION FOR TREATMENT OF AESTHENOPIA

(75) Inventors: Tatsuya Wada, Tokyo (JP); Takashi Mano, Tokyo (JP); Masatoshi Tanouchi, Tokyo (JP)

(73) Assignee: Nihon Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/643,754

(22) PCT Filed: Apr. 25, 2011

(86) PCT No.: PCT/JP2011/060016
§ 371 (c)(1),
(2), (4) Date: Oct. 26, 2012

(87) PCT Pub. No.: WO2011/136159
PCT Pub. Date: Nov. 3, 2011

(65) Prior Publication Data
US 2013/0052286 A1    Feb. 28, 2013

(30) Foreign Application Priority Data
Apr. 28, 2010   (JP) .................. 2010-104355

(51) Int. Cl.
*A01N 65/00*    (2009.01)
(52) U.S. Cl.
USPC ........................................................ 424/725

(58) Field of Classification Search
None
See application file for complete search history.

(56) References Cited

U.S. PATENT DOCUMENTS

| | | |
|---|---|---|
| 2002/0081289 A1 | 6/2002 | Neuhann |
| 2003/0162744 A1 | 8/2003 | Takai et al. |
| 2008/0113935 A1 | 5/2008 | Yedgar et al. |
| 2010/0216741 A1 | 8/2010 | Matsumura et al. |

FOREIGN PATENT DOCUMENTS

| | | |
|---|---|---|
| EP | 1 270 599 | 1/2003 |
| JP | 2002-17295 | 1/2002 |
| JP | 2003-238442 | 8/2003 |
| JP | 2005-287376 | 10/2005 |
| JP | 2006-298791 | 11/2006 |
| JP | 2007-8854 | 1/2007 |
| JP | 2008-297222 | 12/2008 |
| RU | 2 302 231 | 2/2006 |
| WO | WO 2008/059501 | 5/2008 |
| WO | WO 2009/035033 | 3/2009 |

OTHER PUBLICATIONS

International Search Report issued on Sep. 30, 2013 in European Patent Application No. 11 77 4940.

*Primary Examiner* — Michael Meller
(74) *Attorney, Agent, or Firm* — Fanelli Haag & Kilger PLLC

(57) ABSTRACT

This is to provide a novel medicine and a food and a drink composition for treating aesthenopia excellent in improved effect of aesthenopia.
The composition for the treatment of aesthenopia comprises chondroitin sulfate or a salt thereof.

4 Claims, No Drawings

COMPOSITION FOR TREATMENT OF AESTHENOPIA

This application is a U.S. National Stage Application of PCT International Patent Application No. PCT/JP2011/060016, which was filed on Apr. 25, 2011 which claims priority to Japanese Patent Application No. 2010-104355 filed Apr. 28, 2010, the disclosures of each of which is incorporated herein by reference in their entireties.

TECHNICAL FIELD

The present invention relates to a novel composition for the treatment of aesthenopia excellent in improved effects of human aesthenopia, in particular, to a composition for the treatment of aesthenopia which is in a form of a medicine and a food and a drink.

BACKGROUND ART

"Aesthenopia" means a state in which unidentified complaint-like constitutional symptoms such as stiffness in the shoulders or waist, or irritation, etc., appear with the symptoms such as pain and dim of eyes as a result of exploitation of eyes, and one feels fatigue on carrying out an activity even when it can be easily done in a usual state.

As eye diseases, astigmatism, myopia, cataract, glaucoma, etc., have been known, which are caused by hypofunction or malfunction such as aging of eye hall portion, etc., and a treatment therapy can give an effect by eyeglasses or an operation. On the other hand, for a contemporary person, a chance to watch a television or a display of an OA equipment such as a personal computer for a long period of time increases in a home or one's workplace everyday, so that a burden to the eyes markedly increases. Thus, local symptoms such as pain, dim, dazzling or congestion of eyes, and watery eyes, or various constitutional symptoms such as stiffness in the shoulders or waist, irritation, nausea, feeling a heavy head, etc., appear. Aesthenopia is defined to be the conditions that a person is suffered from local symptoms or constitutional symptoms as mentioned above, and the person feels fatigue easily on carrying out a work which can be easily carried out for a healthy person without feeling any fatigue.

Aesthenopia is not a simple eye fatigue, but has characteristics in subsidiary causing various unpleasant symptoms such as stiffness in the shoulders or waist, irritation, nausea, feeling a heavy head, etc.

Human vision (acuity) is an advanced information processing system which is mechanically precise and admits an outer thing as an image through the following mentioned three main steps. (1) A light which is controlled a thickness of the lens and controlled a diaphragm due to high-speed muscular movement of the ciliary body is passed through lens and crystalline lens of eyeball and reached to the retina, (2) the light is converted into an electrical signal through the rod and the cone of the retina, and sent to the visual cortex of the brain through the nerve, and (3) information processing is carried out at the visual cortex to admit it as an image. It is the advanced information processing system which passed through the above-mentioned three steps. The detailed mechanisms are complicated and have not yet been known well. The so-called vision is a function exhibited as a compilation of these functions. It is thought that vision is lowered even if any one of the functions of these three steps is lowered. It has been considered that fatigue is caused as a result of the above, but the onset mechanisms of the aesthenopia having the above-mentioned complicated symptoms, etc., have not yet been known well.

However, in recent years, a person who complains such symptoms is increasing particularly in working young women, so that a health food or a medicine which treats, prevents and improves aesthenopia have been strongly demanded.

As a medicine which professes treatment effects of aesthenopia, Class III medicines such as vitamin B1 agent (ALINAMIN (Takeda Pharmaceutical Co., Ltd.)) and total vitamin agent (QP GOLD KOWA (KOWA Company Ltd.)) are commercially sold for general uses. However, these medicines are approved by merely expecting an anti fatigue effect from a supplemental nutrient function of vitamin B1 as a vitamin. Thus, the effect was approved with a wider scope without any sufficient clinical test as far as aesthenopia is concerned, so that it is the actual situation that they do not show any sufficient effect on the aesthenopia irrespective of the expectation.

Vitamin B1 series medicines had been approved on the effects such as pain relief accompanied by neural transmission, muscular pain, fatigue, etc., from the association that vitamin B is concerned with neural transmission without any sufficient evidence from the viewpoint of modern science, whereas it is unavoidable on a science level of those days. Thus, they are insufficient in the effect and efficacy.

On the other hand, chondroitin sulfate has been admitted to as a medicine and used. That is, sodium chondroitin sulfate has been used as a medicine for the treatment of lumbar pain, joint pain, scapulohumeral periarthritis (frozen shoulder), etc., as an injection solution, and for the protection of a cornea outer layer as an eye drop, and as a medicine for general purpose, it has been used for joint pain and nerve pain as an oral medicine. However, it has never been used for the treatment of aesthenopia as of today.

A food having an effect of improving eye function such as improvement in aesthenopia, etc., has been known, for example, astaxanthin, a blueberry extract, a marigold extract, docosahexaenoic acid, etc. These are formulated in a health food, etc. (Patent literatures 1 to 4).

However, the supplement or the health food into which these eye function-improving agents are formulated shows an effect of improving aesthenopia with a certain extent, but the effect cannot be said to be sufficient, whereby a medicine or a composition of a food and a drink having more excellent treatment, prophylaxis and improved effect of aesthenopia has been demanded.

PRIOR ART LITERATURES

Patent Literatures

[Patent literature 1] JP 2002-17295A
[Patent literature 2] JP 2003-238442A
[Patent literature 3] JP 2005-287376A
[Patent literature 4] JP 2008-297222A

SUMMARY OF THE INVENTION

Problems to be Solved by the Invention

An object of the present invention is to provide a novel composition for the treatment of aesthenopia excellent in a treatment, prophylaxis and improved effect of human aesthenopia.

Means to Solve the Problems

The present inventors have extensively studied to accomplish the above-mentioned objects, and as a result, they have found surprisingly that chondroitin sulfate has an improved effect on aesthenopia, and when astaxanthin, a blueberry extract, a marigold extract, docosahexaenoic acid, hyaluronic acid or a derivative thereof which had been known to have an improved effect is used in combination with chondroitin sulfate, the improved effect on aesthenopia can be further strengthened to accomplish the present invention.

That is, the present invention basically relates to
(1) a composition for the treatment of aesthenopia comprising chondroitin sulfate or a salt thereof; and
(2) a composition for the treatment of aesthenopia comprising chondroitin sulfate or a salt thereof, and at least one selected from the group consisting of astaxanthin, lutein, blueberry extract, a marigold extract, docosahexaenoic acid, hyaluronic acid and a derivative(s) thereof.

Effects of the Invention

According to the present invention, excellent improved effects of aesthenopia can be obtained.

EMBODIMENTS TO CARRY OUT THE INVENTION

The composition for the treatment of aesthenopia of the present invention comprises chondroitin sulfate or a salt thereof being formulated.

Here, the composition for the treatment of aesthenopia means a composition which improves, releases or weakens any of the symptoms caused by aesthenopia, eye fatigue, or stiffness in the shoulders or waist, etc., caused by these symptoms, irritation or feeling a heavy head, etc., in particular, a composition in the form of a medicine or a food and a drink. In the case of the medicine, it is not particularly limited so long as it is in a preparation form of a general medicine. In the case of the food and drink, it is not particularly limited so long as it is in a preparation form of a health food or a general food and drink. Also, in the present invention, it contains a food and a drink themselves as a matter of course, a mixture which is previously mixed to be used for an edible material of a food and a drink, or a preparation product made in a preparation form.

Chondroitin sulfate is a kind of glycosaminoglycan (mucopolysaccharide) which appears in an animal body, and in general, it exists as proteoglycan covalently bonded to a protein which becomes a core which is so-called a core protein. In particular, it exists as proteoglycan which is called aggrecan with a larger amount in an extracellular matrix of cartilage, and widely seen in all of the tissues including a connective tissue such as skin, or in a brain, etc. Almost all the chondroitin sulfate exists as a proteoglycan at the extracellular matrix or the surface of the cells. Chondroitin sulfate exists in cartilage, wall of blood vessel such as artery, the cornea of eyes, skin, the cochlea of the ear with a plenty amount, in particular, chondroitin sulfate is contained in cartilage in an amount of about 20%.

Chondroitin sulfate has a structure in which sulfuric acids are bonded to a sugar chain where two sugars of D-glucuronic acid (GlcA) and N-acetyl-D-galactosamine (GalNAc) are repeated. Among the two sugar units of the "GlcA-GalNAc", there are structural varieties due to addition of the sulfuric acid groups or epimerization (from GlcA to iduronic acid). As for the position of the sulfuric acid group, there are mainly chondroitin-4-sulfate (also called as chondroitin sulfate A) in which the sulfuric acid is added to the 4-position of GalNAc, and chondroitin-6-sulfate (chondroitin sulfate C). In dermatan sulfate (chondroitin sulfate B) in which the 4-position of GalNAc is sulfated, GlcA of chondroitin sulfate is epimerized to become iduronic acid. In the chondroitin sulfate, there are contained chondroitin sulfate E in which both of the 4-position and the 6-position are sulfated, and the structure in which a hydroxyl group of glucuronic acid or iduronic acid is sulfated. In the following Table, a kind of the chondroitin sulfate and the structure and the origin thereof are mentioned. Either of the chondroitin sulfates is contained in the chondroitin sulfate of the present invention.

TABLE 1

| Kind of chondroitin sulfate | | |
|---|---|---|
| Chondroitin sulfate | Recurring disaccharide structure | Origin |
| A | Glucuronic acid-acetylgalactosamine-4-sulfate | Cartilage |
| B | Iduronic acid-2-sulfate-acetylgalactosamine-4-sulfate | Dermatan sulfate, skin |
| C | Glucuronic acid-acetylgalactosamine-6-sulfate | Cartilage |
| D | Glucuronic acid-2-sulfate-acetylgalactosamine-6-sulfate | Dermatan sulfate |
| E | Glucuronic acid-acetylgalactosamine-4,6-disulfate | Squids |

A salt of chondroitin sulfate may be mentioned an alkali metal salt of sodium, potassium, etc., or an alkaline earth metal salt of calcium, magnesium, etc. As a salt, a sodium salt is particularly preferred. The chondroitin sulfate or a salt thereof may be a commercially available product, or may be those prepared by the method mentioned as follows.

The starting materials of the chondroitin sulfate are not limited so long as it is conventionally known starting materials, and may be mentioned cartilage, skin, trachea, scale, etc., of marine products or mammals. The marine products may be mentioned salmon, ray, shark, carp, etc., and the mammals may be mentioned porcine, bovine, whale, etc. Land animals involve risk of BSE, so that fishes are preferred. In view of an amount of the source and the effects, salmon is particularly preferably used as a starting material. Human chondroitin sulfate is type A and type C, shark chondroitin sulfate is type C and type D, and salmon chondroitin sulfate is type A and type C which are the same as human.

The chondroitin sulfate can be extracted and purified from the starting materials by the conventionally known method. As a method for preparing the chondroitin sulfate in general, there have been known the alkali treatment method in which cartilage, skin, trachea, etc., as a starting material is decomposed by an alkali solution and mucopolysaccharides are extracted, the neutral salt treatment method in which it is extracted with a neutral salt solution, the enzyme method in which it is treated by a proteolytic enzyme such as a protease, pronase, alonase, etc.

According to these treatment methods, by cutting the bond between chondroitin sulfate and the core protein, chondroitin sulfate is extracted from the starting materials to obtain an extract. The extract can be used as the chondroitin sulfate in the present invention. As the method of removing impurities from the extract, there may be mentioned the ethanol fractionation treatment, dialysis treatment, ion exchange chromatography treatment, gel filtration treatment and a combination thereof. The purified chondroitin sulfate in which impurities are removed from the extract can be used as the chondroitin sulfate in the present invention.

Salmon-derived chondroitin sulfate can be prepared from nose and head cartilage of salmon. Nose cartilage of salmon has been eaten as HIZU namasu (raw fish seasoned in vinegar) at Hokkaido or North-East (Tohoku) district of Japan. As the method for preparing chondroitin sulfate from nose cartilage of salmon, etc., there have been known the method in which nose cartilage of salmon, etc., is subjected to frost shattering at −30 to 60° C. and delipidation, and then, a solution which has been subjected to an alkali treatment, heating and an enzyme treatment is subjected to an ethanol precipitation, filtration, centrifugation, drying and further, subjected to an ion exchange resin treatment, and freeze-drying to obtain chondroitin sulfate (JP 2001-231497A or JP 2001-247602A) After an enzyme treatment, ultrafiltration is carried out to obtain chondroitin sulfate having a molecular weight of 6000 or higher. The obtained chondroitin sulfate is a complex with a protein, and has the so-called proteoglycan structure. It can be estimated that the effect of the present invention would be improved since the low molecular weight protein or impurities contained therein had been removed. Also, the chondroitin sulfate is a complex structural material with a protein, a part of which has been intricately cut, and as a result, it can be considered that an activity of treatment effect of the invention might be heightened. For making it possible to use as a food, it is required to be noted that "sodium chondroitin sulfate" is not contained therein by refraining from carrying out the operations such as ethanol precipitation and neutralization with caustic soda, etc. In the present invention, from the viewpoint of effects, salmon-derived chondroitin sulfate, particularly salmon-derived chondroitin sulfate extracts prepared by the above-mentioned preparation method is preferably used.

An intake of the chondroitin sulfate or a salt thereof is preferably 100 mg/day or more, more preferably 300 to 1500 mg/day, and particularly preferably 400 to 1000 mg/day.

The chondroitin sulfate or a salt thereof is formulated in the composition for the treatment of aesthenopia preferably with 0.1 to 99.9% by weight, particularly preferably 10 to 90% by weight.

The composition for the treatment of aesthenopia of the present invention may further contain at least one selected from the group consisting of astaxanthin, lutein, a blueberry extract, a marigold extract, docosahexaenoic acid, hyaluronic acid and a derivative(s) thereof. By containing the additional component(s), the composition for the treatment of aesthenopia of the present invention is strengthened in the improved effects of aesthenopia.

Astaxanthin is a kind of carotenoids classified into xanthophylls, and is commercially available as a natural product extracted from fine algae such as *Haematococcus pluvialis* or a synthesized product. It has been known to have an improving effect of eye regulatory function as well as potent antioxidative power.

Lutein is a representative carotenoid alcohol, and distributed in many green-leaved plants or algae. Five kinds of Luteins A, B, D, F and U have been known.

The blueberry extract means, among the plants belonging to *Vaccinium, Ericaceae*, those in which the fruits are ripened with a dark blue-violet and utilized as a fruit tree, and further, bilberry which is generally treated as a family of blueberry is also included in the blueberry of the present invention. Blueberry extracts contain anthocyanin. Anthocyanin is generally contained in the pericarp portion of blueberry, and in bilberry, it is contained in a flesh other than the pericarp with an amount of 3 to 4-fold of the usual blueberry, so that it has been well used as a starting material for the extraction of blueberry. The blueberry extract is commercially available which is obtained by, in general, extracting refrigerated blueberry or crushed bilberry with a solvent such as hydrated ethanol, etc., concentrating the extract, and, if necessary, the extract is purified and evaporated to dryness. In the present invention, such a commercially available product can be preferably used.

In the marigold extract, lutein which is a kind of carotenoids is contained. Lutein exists in macular area or crystalline lens (lens) of eyes with zeaxanthin, shows a function like SOD (superoxide dismutase), and it has been said that it removes active oxygen generated in the eyes.

Marigold is a kind of *Asteraceae*, and the marigold extract contain lutein which is a kind of carotenoid extracted from petals of marigold. Lutein exists in macular area or crystalline lens (lens) of eyes with zeaxanthin, shows a function like SOD (super-oxide dismutase), and it has been said that it removes active oxygen generated in the eyes. Dried petals of marigold are extracted with an organic solvent such as hexane, etc., and then, the organic solvent is removed from the extract. Those in which the extract is hydrolyzed, purified and crystallized to contain about 20% of lutein have been commercially sold, which are preferably used in the present invention.

Docosahexaenoic acid is a highly unsaturated fatty acid belonging to a n-3 series, in natural, it exists as a constitutional fatty acid of triglyceride. The docosa-hexaenoic acid is also contained in phospholipids of retina and optic nerve, and it has been said to have an important role for transmission of information in vision. The docosahexaenoic acid or a derivative thereof to be used in the present invention may be mentioned, for example, oils and fats extracted from a fish oil which is extracted from tuna, mackerel, pacific saury, horse mackerel, etc., fatty acids mixture obtained by hydrolyzing these oils and fats, a lower alcohol ester obtained by esterification reaction of these fatty acids mixtures and a lower alcohol such as ethanol, etc., and those in which oils and fats containing these docosahexaenoic acid or a derivative thereof are purified by various kinds of purification techniques, and these can be preferably used.

Hyaluronic acid is a polysaccharide comprising two saccharides of glucuronic acid and N-acetylglucosamine as recurring constitutional units, and as the salt of the hyaluronic acid, any salts can be used so long as it is acceptable as a medicine or a food such as sodium, potassium, calcium, etc. The hyaluronic acid or a salt thereof can be generally obtained by using a biological tissue such as cockscomb, eye ball, skin, cartilage, etc., or a culture broth obtained by culturing hyaluronic acid-producing microorganisms such as a microorganism belonging to the genus of *Streptococcus*, etc. as a starting material, and extracting from these starting materials and farther purifying the same. As the hyaluronic acid or a salt thereof of the present invention, either of a crude extract or a purified product may be used, preferably used is a purified product, and more specifically a hyaluronic acid or a salt thereof having a purity of 90% or higher is preferred. This is because the hyaluronic acid or a salt thereof having a purity of 90% or higher can easily provide a preferable food and drink which do not occur coloring or any had order during the preservation thereof when it is used as one of the starting materials of a food and a drink. The molecular weight of the hyaluronic acid or a salt thereof to be used in the present invention is not particularly limited.

In the composition for the treatment of aesthenopia of the present invention, an intake of the chondroitin sulfate is preferably 100 mg or more, particularly 500 mg or more per day for an average adult (about 60 kg). In the composition for the treatment of aesthenopia of the present invention, when one or more selected from the group consisting of astaxanthin, lutein, the blueberry extract, the marigold extract, docosahexaenoic acid, hyaluronic acid or a derivative thereof is formulated in addition to the chondroitin sulfate, each intake amount is preferably 500 mg or more of chondroitin sulfate, 0.01 mg or more of astaxanthin in terms of astaxanthin free material, 10 mg or more of a blueberry extract in terms of anthocyanin, 0.1 mg or more of a marigold extract in terms of lutein, 10 mg or more of docosahexaenoic acid or a derivative thereof in terms of docosahexaenoic acid, 5 mg or more of hyaluronic acid or a salt thereof for an average adult person (about 60 kg) per day. Each intake amount is particularly preferably 500 mg or more of chondroitin sulfate, 0.1 mg or more of astaxanthin in terms of astaxanthin free material, 30 mg or more of a blueberry extract in terms of anthocyanin, 0.2 mg or more of a marigold extract in terms of lutein, 100 mg or more of docosahexaenoic acid or a derivative thereof in terms of docosahexaenoic acid, and 25 mg or more of hyaluronic acid or a salt thereof for an average adult person (about 60 kg) per day.

In the present invention, the upper limits of the respective formulation amounts are not regulated, but when they are too much, an effect in comply with the formulation amount, i.e., the intake, cannot be obtained. Thus, each intake amount is 1500 mg or less, more preferably 1000 mg or less of chondroitin sulfate, 20 mg or less of astaxanthin in terms of astaxanthin free material, preferably 150 mg or less, more preferably 100 mg or less of the blueberry extract in terms of anthocyanin, preferably 10 mg or less, more preferably 8 mg or less of the marigold extract in teens of lutein, preferably 200 mg or less, more preferably 150 mg or less of docosahexaenoic acid or a derivative thereof in terms of docosahexaenoic acid, and preferably 1500 mg or less, more preferably 1000 mg or less of hyaluronic acid or a salt thereof for an average adult person (about 60 kg) per day.

To the composition for the treatment of aesthenopia of the present invention, various nutrient components or various kinds of food starting materials such as excipient, etc., can be added by optional selection within the range which does not impair the effects of the present invention. There may be mentioned, for example, vitamins such as vitamin B2, vitamin B12, vitamin E, ascorbic acid or a salt thereof, etc., nutrient components such as nucleic acid, collagen peptide, etc., mineral components such as iron, calcium, zinc, etc., highly unsaturated fatty acids such as eicosapentaenoic acid, arachidonic acid, etc., functional oils and fats such as eggyolk recithin, soybean recithin, eggyolk oil, etc., and excipients such as an extender, a binder, a lubricant, a preservative, an antioxidant, a flavor, etc.

The composition for the treatment of aesthenopia of the present invention can be in the form of a medicine. The medicine includes an injection and an oral agent. As the medicine, the compound itself, or a composition which is in combination with the conventionally known medical additives according to the conventional method may be used, and various kinds of preparations are possible. For example, as an orally administrating agent, there may be mentioned a solid agent such as tablets, granules, powders, capsules, soft capsules, etc., a liquid agent such as a solution, a suspension, an emulsion, etc., a freeze-dried preparation, etc., and as a parenterally administrating agent, there may be mentioned, in addition to an injection, a suppository, a spray, a cutaneous absorption agent, etc. These preparations can be prepared according to the conventional method to be used for preparation. The above-mentioned medical additives may be mentioned, for example, glucose, lactose, sucrose, starch, mannitol, crystalline cellulose, dextrin, aliphatic acid glyceride, polyethylene glycol, hydroxyethyl starch, ethylene glycol, polyoxyethylene sorbitan fatty acid ester, amino acid, albumin, water, physiological saline, etc. Also, if necessary, other conventionally used additives such as a stabilizer, a lubricant, a humectant, an emulsifier, a binder, etc., may be optionally added.

The chondroitin sulfate of the present invention, in particular, a salmon-derived chondroitin sulfate is considered to be highly safe since fish meat of salmon has been eaten from ancient times as well as a whole body thereof including bones and skins for a long period of time, so that the composition for the treatment of aesthenopia of the present invention can be used as various kinds of foods and drinks. As the food and chink, a final form can be made by the chondroitin sulfate itself alone, or by adding the chondroitin sulfate to the other foods and drinks.

The food and drink can be taken in the form of a functional food for the purpose of improving aesthenopia. The functional food can be positioned as foods for specified health uses, a nutritional functional food, or a health food.

In the functional food which is one of the embodiments of the present invention, those in which the chondroitin militate is contained, and displayed that they have an effect of improving aesthenopia are contained.

As the food and drink which is the composition for the treatment of aesthenopia of the present invention, there may be used, for example, those in which a suitable additive(s) is/are added to the chondroitin sulfate, and formed into an edible form such as granular, powder, a tablet, a capsule, a paste state, etc., by using a conventional means. This functional food can be applied directly for food, or may be used by adding to various foods (for example, ham, sausage, boiled fish paste, tubular fish paste, bread, butter, powdered milk, confectionery, etc.), or, may be used by adding to drinks such as water, alcoholic drinks, fruit juice, milk, soft drink, etc.

An intake of the chondroitin sulfate of the present invention in the form of a food may be optionally selected and determined depending on the age, body weight, symptoms, intake schedule of the object, and form of the preparation, etc., and, for example, it is 0.01 to 10 g/kg body weight per day as a dry powder equivalent amount.

The composition for the treatment of aesthenopia of the present invention can be made an antifatigue action agent and/or a stamina reinforcing action agent. A suitable additive(s) such as a mold-solidification promoter, a solubilizing agent, a nutrient, etc., is/are added to the chondroitin sulfate, and used by forming into an edible form such as granular, powder, a tablet, a capsule, a paste state, etc., using a conventional means. Also, it may be used by adding to an animal food and a pet food, or may be added to drinking water such as water, etc.

An intake of the chondroitin sulfate of the present invention in the form of a food may be optionally selected and determined depending on the age, body weight, symptoms, intake schedule of the animal, and form of the preparation, etc., and, for example, it is 0.01 to 10 g/60 kg body weight per day as a dry powder equivalent amount.

The food and drink as the composition for the treatment of aesthenopia of the present invention may include, for example, butter, bread, chocolate, pudding, noodles, tea, coffee, cocoa, drink, fruit juice drink, sport drink, soft drink, etc. The drink is preferably an aqueous drink such as mineral water and carbonated water, a tea series drink such as green tea, tea and oolong tea, a milky drink such as a milk and yogurt, a juice series drink such as fruit juice and vegetable juice, a drink containing coffee or cocoa, various kinds of drinks such as sport drink and nutritional drink, a healthy drink containing vinegar, etc., an alcohol series drink such as Japanese rice wine, Japanese spirits, beer and wine, etc.

For preparing the composition for the treatment of aesthenopia according to the present invention, when it is made in a form of a gelatin capsule, an aqueous gelatin solution wherein a gelatin and glycerin which are components for an encapsulating material had been dissolved in water is firstly prepared, and a contained material is prepared by uniformly mixing the respective components of the present invention and other nutrient components or an excipient in an oily base material. Then, while molding a capsule from the above-mentioned aqueous gelatin solution by a capsule filling machine, the above-mentioned contained material is filled therein to prepare a capsule type medicine and food and drink composition for treating aesthenopia of the present invention.

Next, the present invention will be explained in more detail by referring to Examples and Test examples. The present invention is not limited by these.

EXAMPLES

Example 1

Salmon-derived chondroitin sulfate extract was prepared according to the following preparation method. Head cartilage of salmon containing nose cartilage of the same was washed and contaminated materials were removed. Frozen material at −50° C. was crushed by a cutting mill type crusher, heated and subjected to an enzyme treatment. The solution obtained by subjecting to centrifugation was passed through an ultrafiltration device, and the resulting liquid was spray dried to obtain powder of chondroitin sulfate extract.

Tablets containing salmon-derived chondroitin sulfate were prepared.

Components and contents thereof per a tablet (250 mg) are as follows.

| | |
|---|---|
| Salmon-derived chondroitin sulfate extract powder | 125.0 mg (50%) |
| Lactose | 50.0 mg (20%) |
| Crystalline cellulose | 67.5 mg (27%) |
| Fine grain silicon dioxide | 2.5 mg (1.0%) |
| Sucrose fatty acid ester | 5.0 mg (2.0%) |

Example 2

To 100 ml of warm water placed in a bowl was added a pack of JELLY ACE (available from House Foods Corp.) and dissolved. Further, a liquid in which 4 g of salmon-derived chondroitin sulfate extract powder had been dispersed in 300 ml of warm water was added to the above solution and mixed well. This was flown into a mold with a shape of cup having 50 ml, and placed in a refrigerator about 2 hours or longer to prepare a solid state jelly.

Test example 1

Treatment Test of Aesthenopia (Tablet)

To investigate the effects of taking chondroitin sulfate on aesthenopia and a regulatory function, tests were carried out by the following methods.
1. Test Sample Test sample is a tablet containing salmon-derived chondroitin sulfate extract powder prepared in Example 1.
2. Subject The eleven subjects are 30-old or more and 40-old or less Japanese male and female at the time of the agreement acquisition, who satisfy selection criteria that he/she usually feels fatigue of eyes, and usually uses a personal computer (work that requires precision, etc., is included) (6 hours or longer in average/1 day) including a VDT operation.
3. Protocol For 4 weeks, 4 tablets of Test sample (amount of chondroitin sulfate: 500 mg) were orally taken to the testees with water and without chewing after supper every day. After 4 weeks, according to ethical principles based on Declaration of Helsinki, an effect on a regulatory function accompanied by aesthenopia and a recovery effect on a regulatory function provided by a rest after the VDT operation were inspected by an open test.
4. Test Results Whereas the present test was started with 11 members of subjects, 1 member was declined due to one's own convenience during the test, so that, in the following, 10 members were made analysis objects.
(1) Transition (Change) of Questionnaire Survey (VAS System) (with a Lapse of Time)

With regard to the respective test items, these were judged from "I think so" to "I do not think so" with a scale of 0 to 100.
(a) Eyes Get Tired It was 79.7±16.3 before intake of Test sample, 59.2±28.5 after 2 weeks from the intake, and 46.5±38.8 after 4 weeks from the intake. As compared with before intake, it was −20.5 after 2 weeks from the intake, and −33.2 after 4 weeks from the intake, so that significant difference was admitted after 4 weeks from the intake (P=0.006).
(b) Eyes are Pressed It was 313±32.7 before intake of Test sample, 38.2±37.9 after 2 weeks from the intake, and 27.1±34.1 after 4 weeks from the intake. As compared with before intake, it was +6.9 after 2 weeks from the intake, and −4.2 after 4 weeks from the intake, so that no significant difference was admitted.
(c) Eyes are Cracked It was 265±26.8 before intake of Test sample, 20.6±30.0 after 2 weeks from the intake, and 15.2±23.3 after 4 weeks from the intake. As compared with before intake, it was −5.9 after 2 weeks from the intake, and −11.3 after 4 weeks from the intake, so that no significant difference was admitted,
(d) Eyes are Dull It was 51.7±31.5 before intake of Test sample, 43.4±34.6 after 2 weeks from the intake, and 32.6±37.0 after 4 weeks from the intake. As compared with before intake, it was −8.3 after 2 weeks from the intake, and −19.1 after 4 weeks from the intake, so that no significant difference was admitted.
(e) Eyes Get Dry It was 49.6±34.6 before intake of Test sample, 37.1±36.1 after 2 weeks from the intake, and 27.9±37.1 after 4 weeks from the intake. As compared with before intake, it was −12.5 after 2 weeks from the intake, and −21.7 after 4 weeks from the intake, so that significant difference was admitted after 4 weeks from the intake (P=0.004).
(f) Eyes Dim It was 60.8±34.7 before intake of Test sample, 39.7±36.5 after 2 weeks from the intake, and 24.8±35.1 after 4 weeks from the intake. As compared with before intake, it was −21.1 after 2 weeks from the intake, and −36.0 after 4 weeks from the intake, so that significant difference was admitted after 4 weeks from the intake (P=0.001).
(g) Eyes are Congested It was 50.9±36.3 before intake of Test sample, 41.4±36.9 after 2 weeks from the intake, and 22.3±35.7 after 4 weeks from the intake. As compared with before intake, it was −9.5 after 2 weeks from the intake, and −28.6 after 4 weeks from the intake, so that significant difference was admitted after 4 weeks from the intake (P<0.001).

(h) Thing Flickers

It was 40.4±32.0 before intake of Test sample, 20.0±23.6 after 2 weeks from the intake, and 10.9±19.6 after 4 weeks from the intake. As compared with before intake, it was −20.4 after 2 weeks from the intake, and −29.5 after 4 weeks from the intake, so that significant difference was admitted after 2 weeks from the intake (P=0.025), and after 4 weeks from the intake (P=0.002).

(i) Thing Looks Doable

It was 41.9±40.1 before intake of Test sample, 21.5±31.5 after 2 weeks from the intake, and 21.7±33.9 after 4 weeks from the intake. As compared with before intake, it was −20.4 after 2 weeks from the intake, and −20.2 after 4 weeks from the intake, so that no significant difference was admitted.

(j) Shoulder Grows Stiff

It was 74.0±28.6 before intake of Test sample, 61.6±40.0 after 2 weeks from the intake, and 61.9±41.2 after 4 weeks from the intake. As compared with before intake, it was −1.2.4 after 2 weeks from the intake, and −12.1 after 4 weeks from the intake, so that no significant difference was admitted.

(2) Transition (Change) of Questionnaire Survey (VAS System) (VDT Load)

In the observation before intake of Test sample, and after 4 weeks of the intake, a VDT operation was carried out by the following mentioned method.

Among the alphabets A to Z displayed on a display, R was clicked by a mouse (the display is changed by every click). When one clicked an alphabet other than R, it is made an error, and a number of correct answer and a number of incorrect answer were counted.

The above-mentioned operation was carried out for 30 minutes.

After 30 minutes from starting the operation, a continuous near point measurement, a dynamic vision measurement, and a VAS questionnaire survey were carried out.

After completion of the inspection, an eye mask was put on, and the person has a rest staying quiet on a sofa for 30 minutes, the eye mask was taken off and staying quiet for 1 minute, then, a continuous near point measurement, a dynamic vision measurement and a VAS questionnaire survey were carried out.

With regard to the respective test items, these were judged from "I think so" to "1 do not think so" with a scale of 0 to 100.

(a) Eyes Get Tired

It was 79.7±16.3 before intake of Test sample and before loading, 70.7±32.1 immediately after the loading, and 30.6±23.1 after the rest for 30 minutes. As compared with before loading, it was −9.0 immediately after the loading, and −49.1 after the rest for 30 minutes, so that significant difference was admitted after the rest for 30 minutes (P<0.001).

It was 46.5±38.8 after 4 weeks from the intake of Test sample and before loading, 59.4±38.0 immediately after the loading, and 34.1±32.5 after the rest for 30 minutes. As compared with before loading, it was +12.9 immediately after the loading, and −12.4 after the rest for 30 minutes, so that significant difference was admitted immediately after the loading (P=0.034), and after the rest for 30 minutes (P=0.042).

By the comparison before intake of Test sample and after 4 weeks from the intake of the same, significant difference was admitted before loading (P=0.011).

(b) Eyes are Pressed

It was 31.3±32.7 before intake of Test sample and before loading, 34.1±28.9 immediately after the loading, and 20.4±21.2 after the rest for 30 minutes. As compared with before loading, it was +2.8 immediately after the loading, and −10.9 after the rest for 30 minutes, so that no significant difference was admitted.

It was 27.1±34.1 after 4 weeks from the intake of Test sample and before loading, 36.5±35.5 immediately after the loading, and 18.9±28.1 after the rest for 30 minutes. As compared with before loading, it was +9.4 immediately after the Loading, and −8.2 after the rest for 30 minutes, so that no significant difference was admitted.

By the comparison before intake of Test sample and after 4 weeks from the intake of the same, no significant difference was admitted.

(c) Eyes are Cracked

It was 26.5±26.8 before intake of Test sample and before loading, 36.4±37.2 immediately after the loading, and 17.6±22.2 after the rest for 30 minutes. As compared with before loading, it was +9.9 immediately after the loading, and −8.9 after the rest for 30 minutes, so that no significant difference was admitted.

It was 15.2±23.3 after 4 weeks from the intake of Test sample and before loading, 29.2±30.6 immediately after the loading, and 12.0±14.8 after the rest for 30 minutes. As compared with before loading, it was +14.0 immediately after the loading, and −3.2 after the rest for 30 minutes, so that no significant difference was admitted.

By the comparison before intake of Test sample and after 4 weeks from the intake of the same, significant difference was admitted before loading (P=0.023).

(d) Eyes are Dull

It was 51.7±31.5 before intake of Test sample and before loading, 47.8±38.4 immediately after the loading, and 26.1±26.2 after the rest for 30 minutes. As compared with before loading, it was −3.9 immediately after the loading, and −25.6 after the rest for 30 minutes, so that no significant difference was admitted.

It was 32.6±37.0 after 4 weeks from the intake of Test sample and before loading, 40.0±36.8 immediately after the loading, and 22.3±27.9 after the rest for 30 minutes. As compared with before loading, it was +7.4 immediately after the loading, and −10.3 after the rest for 30 minutes, so that no significant difference was admitted.

By the comparison before intake of Test sample and after 4 weeks from the intake of the same, no significant difference was admitted.

(e) Eyes Get Dry

It was 49.6±34.6 before intake of Test sample and before loading, 54.4±41.6 immediately after the loading, and 28.4±33.9 after the rest for 30 minutes. As compared with before loading, it was +4.8 immediately after the loading, and −21.2 after the rest for 30 minutes, so that significant difference was admitted after the rest for 30 minutes (P=0.020).

It was 27.9±37.1 after 4 weeks from the intake of Test sample and before loading, 39.6±42.7 immediately after the loading, and 21.8±26.5 after the rest for 30 minutes. As compared with before loading, it was +11.7 immediately after the loading, and −6.1 after the rest for 30 minutes, so that no significant difference was admitted.

By the comparison before intake of Test sample and after 4 weeks from the intake of the same, significant difference was admitted before loading (P=0.008), (f) Eyes Dim It was 60.8±34.7 before intake of Test sample and before loading, 40.5±32.3 immediately after the loading, and 12.5±12.1 after the rest for 30 minutes. As compared with before loading, it was −20.3 immediately after the loading, and −48.3 after the rest for 30 minutes, so that significant difference was admitted after the rest for 30 minutes (P<0.001).

It was 24.8±35.1 after 4 weeks from the intake of Test sample and before loading, 22.7±27.2 immediately after the loading, and 20.1±30.7 after the rest for 30 minutes. As compared with before loading, it was −2.1 immediately after the loading, and −4.7 after the rest for 30 minutes, so that no significant difference was admitted.

By the comparison before intake of Test sample and after 4 weeks from the intake of the same, significant difference was admitted before loading (P=0.003).

(g) Eyes are Congested

It was 50.9±36.3 before intake of Test sample and before loading, 40.5±34.0 immediately after the loading, and 36.9±41.2 after the rest for 30 minutes. As compared with before loading, it was −10.4 immediately after the loading, and −14.0 after the rest for 30 minutes, so that no significant difference was admitted.

It was 22.3±35.7 after 4 weeks from the intake of Test sample and before loading, 35.2±35.8 immediately after the loading, and 30.3±37.2 after the rest for 30 minutes. As compared with before loading, it was +12.9 immediately after the loading, and +8.0 after the rest for 30 minutes, so that significant difference was admitted immediately after the loading (P=0.011).

By the comparison before intake of Test sample and after 4 weeks from the intake of the same, significant difference was admitted before loading (P=0.008).

(h) Thing Flickers

It was 40.4±32.0 before intake of Test sample and before loading, 27.7±30.3 immediately after the loading, and 7.80±7.08 after the rest for 30 minutes. As compared with before loading, it was −12.7 immediately after the loading, and −32.6 after the rest for 30 minutes, so that significant difference was admitted after the rest for 30 minutes (P=0.003).

It was 10.9±19.5 after 4 weeks from the intake of Test sample and before loading, 17.7±23.5 immediately after the loading, and 6.30±10.02 after the rest for 30 minutes. As compared with before loading, it was +6.8 immediately after the loading, and −4.6 after the rest for 30 minutes, so that no significant difference was admitted.

By the comparison before intake of Test sample and after 4 weeks from the intake of the same, so that significant difference was admitted before loading (P=0.007).

(i) Thing Looks Double

It, was 41.9±40.1 before intake of Test sample and before loading, 22.2±31.8 immediately after the loading, and 7.80±8.72 after the rest for 30 minutes. As compared with before loading, it was −19.7 immediately after the loading, and −34.1 after the rest for 30 minutes, so that significant difference was admitted after 30 minutes from the rest (P=0.009).

It was 21.7±33.9 after 4 weeks from the intake of Test sample and before loading, 19.8±27.0 immediately after the loading, and 9.70±10.88 after the rest for 30 minutes. As compared with before loading, it was −1.9 immediately after the loading, and −12.0 after the rest for 30 minutes, so that no significant difference was admitted.

By the comparison before intake of Test sample and after 4 weeks from the intake of the same, no significant difference was admitted.

(j) Shoulder Grows Stiff

It was 74.0±28.6 before intake of Test sample and before loading, 81.2±20.0 immediately after the loading, and 71.3±27.4 after the rest for 30 minutes. As compared with before loading, it was +7.2 immediately after the loading, and −2.7 after the rest for 30 minutes, so that no significant difference was admitted.

It was 61.9141.2 after 4 weeks from the intake of Test sample and before loading, 74.5±33.3 immediately after the loading, and 63.0±37.2 after the rest for 30 minutes. As compared with before loading, it was +12.6 immediately after the loading, and +1.1 after the rest for 30 minutes, so that significant difference was admitted immediately after the loading (P=0.042).

By the comparison before intake of Test sample and after 4 weeks from the intake of the same, no significant difference was admitted.

(3) Transition of Continuous Near Point Measurement (Measured Right and Left) (with a Lapse of Time)

As visual system fatigue caused by a VDT operation, etc., there is lowering in an eye regulatory function due to fatigue of a ciliary muscle which conducts adjustment of a lens. When seeing a near object, a ciliary muscle becomes tense to thicken a lens, and when seeing a long distance conversely, the ciliary muscle loosens to make the lens thin. It has been known that these mechanisms of focus adjustment are temporarily lowered due to visual system fatigue, and an evaluation of aesthenopia utilizing the above has been reported. For the purpose of measuring the focus adjustment function objectively, an appeared near point and disappeared near point were measured by using a continuous near point optometer (KOWA NP Accommodometer manufactured by KOWA Company Ltd.) to carry out evaluation of visual system fatigue.

(a) Appearance (Right)

It was 206±46 mm before intake of Test sample, 171±44 mm after intake of the same for 2 weeks, and 145±27 mm after intake of the same for 4 weeks. As compared with before intake, it was −35 mm after 2 weeks from the intake, and −61 mm after 4 weeks from the intake, so that significant difference was admitted after 2 weeks from the intake (P=0.020), and after 4 weeks from the intake (P<0.001).

(b) Appearance (Left)

It was 179±33 mm before intake of Test sample, 170±34 mm after 2 weeks from the intake, and 158±28 mm after 4 weeks from the intake. As compared with before intake, it was −9 mm after 2 weeks from the intake, and −21 mm after 4 weeks from the intake, so that significant difference was admitted after 4 weeks from the intake (P=0.014).

(c) Disappearance (Right)

It was 185±50 mm before intake of Test sample, 181±63 mm after 2 weeks from the intake, and 193±59 mm after 4 weeks from the intake. As compared with before intake, it was −4 mm after 2 weeks from the intake, and +8 mm after 4 weeks from the intake, so that no significant difference was admitted.

(d) Disappearance (Left)

It was 201±66 mm before intake of Test sample, 176±57 turn after 2 weeks from the intake, and 191±57 mm after 4 weeks from the intake. As compared with before intake, it was −25 mm after 2 weeks from the intake, and −10 mm after 4 weeks from the intake, so that no significant difference was admitted.

(4) Transition of Continuous Near Point Measurement (Measured Right and Left) (VDT Loading)

(a) Appearance (Right)

It was 206±46 mm before intake of Test sample and before loading, 205±78 mm immediately after the loading, and 188±55 mm after the rest for 30 minutes. As compared with before loading, it was −1 mm immediately after the loading, and −18 mm after the rest for 30 minutes, so that no significant difference was admitted.

It was 145±27 mm after 4 weeks from the intake of Test sample and before loading, 160±42 min immediately after the loading, and 169±30 mm after the rest for 30 minutes. As compared with before loading, it was +15 mm immediately after the loading, and +24 mm after the rest for 30 minutes, so that significant difference was admitted immediately after the loading (P=0.044), and after the rest for 30 minutes (P=0.001).

By the comparison before intake of Test sample and after 4 weeks from the intake of the same, significant difference was admitted before loading (P=0.001), and immediately after the loading (P=0.044).

A relative value (%) obtained by dividing the value after the intake of Test sample by the value before intake was 99±22 before intake and immediately after the loading, and 92±19 after the rest for 30 minutes.

It was 109±13 after 4 weeks from the intake of Test sample and immediately after the loading, and 118±13 after the rest for 30 minutes.

By the comparison before intake of Test sample and after 4 weeks from the intake of the same, significant difference was admitted after the rest for 30 minutes (P=0.017).

(b) Appearance (Left)

It was 179±33 Trim before intake of Test sample and before loading, 195±54 mm immediately after the loading, and 177±32 mm after the rest for 30 minutes. As compared with before loading, it was +16 mm immediately after the loading, and −2 mm after the rest for 30 minutes, so that no significant difference was admitted.

It was 158±28 mm after 4 weeks from the intake of Test sample and before loading, 167±32 mm immediately after the loading, and 168±33 mm after the rest for 30 minutes. As compared with before loading, it was +9 mm immediately after the loading, and +10 mm after the rest for 30 minutes, so that no significant difference was admitted.

By the comparison before intake of Test sample and after 4 weeks from the intake of the same, significant difference was admitted before loading (P=0.027), and immediately after the loading (P=0.045).

A relative value (%) obtained by dividing the value after the intake of Test sample by the value before intake was 108±14 before intake and immediately after the loading, and 100±10 after the rest for 30 minutes.

It was 105±6 after 4 weeks from the intake of Test sample and immediately after the loading, and 106±9 after the rest for 30 minutes.

By the comparison before intake of Test sample and after 4 weeks from the intake of the same, no significant difference was admitted.

(c) Disappearance (Right)

It was 185±50 mm before intake of Test sample and before loading, 202±53 mm immediately after the loading, and 185±64 mm after the rest for 30 minutes. As compared with before loading, it was +17 mm immediately after the loading, and ±0 mm after the rest for 30 minutes, so that no significant difference was admitted.

It was 193±59 mm after 4 weeks from the intake of Test sample and before loading, 187±58 mm immediately after the loading, and 186±62 min after the rest for 30 minutes. As compared with before loading, it was −6 mm immediately after the loading, and −7 mm after the rest for 30 minutes, so that no significant difference was admitted.

By the comparison before intake of Test sample and after 4 weeks from the intake of the same, no significant difference was admitted.

A relative value (%) obtained by dividing the value after the intake of Test sample by the value before intake was 111±19 before intake and immediately after the loading, and 101±24 after the rest for 30 minutes.

It was 97±13 after 4 weeks from the intake of Test sample and immediately after the loading, and 97±17 after the rest for 30 minutes.

By the comparison before intake of Test sample and after 4 weeks from the intake of the same, significant difference was admitted immediately after the loading (P=0.007).

(d) Disappearance (Left)

It was 201±66 mm before intake of Test sample and before loading, 197±61 mm immediately after the loading, and 197±73 mm after the rest for 30 minutes. As compared with before loading, it was −4 mm immediately after the loading, and −4 mm after the rest for 30 minutes, so that no significant difference was admitted.

It was 191±57 mm after 4 weeks from the intake of Test sample and before loading, 190±52 mm immediately after the loading, and 192±67 mm after the rest for 30 minutes. As compared with before loading, it was −1 mm immediately after the loading, and +1 mm after the rest for 30 minutes, so that no significant difference was admitted.

By the comparison before intake of Test sample and after 4 weeks from the intake of the same, no significant difference was admitted.

A relative value (%) obtained by dividing the value after the intake of Test sample by the value before intake was 101±19 before intake and immediately after the loading, and 99±18 after the rest for 30 minutes.

It was 101±14 after 4 weeks from the intake of Test sample and immediately after the loading, and 102±27 after the rest for 30 minutes.

By the comparison before intake of Test sample and after 4 weeks from the intake of the same, no significant difference was admitted.

(5) Transition of 3 Meter Vision (Acuity)

(a) VD (Right)

It was 0.575±0.449 before intake of Test sample, 0.705±0488 after 2 weeks from the intake, and 0.710±0.484 after 4 weeks from the intake. As compared with before intake, it was +0.130 after 2 weeks from the intake, and +0.135 after 4 weeks from the intake, so that significant difference was admitted after 2 weeks from the intake (P=0.005), and after 4 weeks from the intake (P=0.004).

(b) VS (Left)

It was 0.700±0.435 before intake of Test sample, 0.780±0.408 after 2 weeks from the intake, and 0.840±0.389 after 4 weeks from the intake. As compared with before intake, it was +0.080 after 2 weeks from the intake, and +0.140 after 4 weeks from the intake, so that significant difference was admitted after 4 weeks from the intake (P=0.023).

(6) Transition of VDT Operation Efficiency

Among the alphabets A to Z displayed on a display, when one clicked R by a mouse, it is made an error if one clicked an alphabet other than R, and a number of correct answer and a number of incorrect answer were counted.

(a) Number of Correct Answer

It was 796±181 before intake of Test sample, and 875±171 after 4 weeks from the intake. As compared with before intake, it was +79 after 4 weeks from the intake, so that significant difference was admitted (P=0.003).

(b) Number of Incorrect Answer

It was 3.10±3.63 before intake of Test sample, and 2.70±2.26 after 4 weeks from the intake. As compared with before intake, it was −0.40 after 4 weeks from the intake, so that no significant difference was admitted, 5. Conclusion From the results mentioned above, with regard to the effects due to oral intake of the salmon-derived chondroitin sulfate on aesthenopia and the eye regulatory function, significant improvements were observed after 2 weeks from the intake or after 4 weeks from the intake on eye fatigue, drying, dim, congestion and flickering which are chronic subjective symptoms. In appearance of a continuous near point optometer in the present test, significant improvement was observed after 2 weeks from the intake or after 4 weeks from the intake. Also, with regard to the 3 meter vision, both of right and left were significantly high values after 2 weeks from the intake or after 4 weeks from the intake.

Accordingly, due to the intake of Test sample, an improved effect on chronic aesthenopia and a recovery effect on a regulatory function accompanied by improvement in aesthenopia were suggested.

Test example 2

Treatment Test of Aesthenopia (Jelly)

In place of Test sample (4 tablets) in Example 1, the same tests were carried out except for taking the jelly of Example 2. As a result, with regard to (1) transition of questionnaire survey (VAS system) (with a lapse of time), significant improvement effects were admitted on (a) eyes get tired, (b) eyes are pressed, (c) eyes are cracked, (d) eyes are dull, (e) eyes get dry, (f) eyes dim, (g) eyes are congested, etc., before and after the test. Significant differences were admitted on (2) transition of continuous near point measurement (measured Right and Left) (with a lapse of time), (a) appearance (Right), (b) appearance (Left), (3) transition of the 3 meter vision, (a) VD (Right), (b) VS (Left), and (4) transition of VDT operation efficiency, (a) number of correct answers.

From the results mentioned above, due to the intake of the jelly containing the salmon-derived chondroitin sulfate extract powder, with regard to the effects exerted on aesthenopia and an eye regulatory function, significant improvements were observed after 2 weeks from the intake on eye fatigue, drying, dim, congestion and flickering which are chronic subjective symptoms in appearance of a continuous near point meter in the present test, significant improvement was observed after 2 weeks from the intake or after 4 weeks from the intake. Also, with regard to the 3 meter vision, both of right and left were significantly high values after 2 weeks from the intake or after 4 weeks from the intake.

Accordingly, due to intake of Test sample (salmon-derived chondroitin sulfate-containing jelly), an improved effect on chronic aesthenopia and recovery of a regulatory function accompanied by improvement in aesthenopia were suggested.

UTILIZABILITY IN INDUSTRY

According to the present invention, the novel composition for the treatment of aesthenopia which is excellent in treatment, prophylaxis and improved effects in human aesthenopia can be provided.

The invention claimed is:

1. A method of treating a human suffering from aesthenopia consisting essentially of orally administering to said human a therapeutically effective amount of salmon chondroitin sulfate or a salt thereof and one or more additional components selected from the group consisting of astaxanthin, lutein, blueberry extract, marigold extract, docosahexaenoic acid, hyaluronic acid and mixtures thereof to treat said aesthenopia in said human.

2. The method of treating a human suffering from aesthenopia of claim 1, wherein the oral administration does not include glycyrrhizic acid or an animal liver.

3. The method of treating a human suffering from aesthenopia of claim 1, wherein the oral administration is in a pharmaceutically acceptable form.

4. The method of treating a human suffering from aesthenopia of claim 1, wherein the oral administration is via a food or drink.

* * * * *